US012285422B2

(12) United States Patent
Eder et al.

(10) Patent No.: US 12,285,422 B2
(45) Date of Patent: Apr. 29, 2025

(54) USES OF PIPERIDINYL-INDOLE DERIVATIVES

(71) Applicant: NOVARTIS AG, Basel (CH)

(72) Inventors: Jorg Eder, Rheinfelden (DE); Richard Alexander Harrison, Shropshire (GB); Boerje Haraldsson, Riehen (CH); Anna Svenja Shchubart Wellensiek, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/589,281

(22) Filed: Jan. 31, 2022

(65) Prior Publication Data
US 2022/0152011 A1 May 19, 2022

Related U.S. Application Data

(63) Continuation of application No. 16/642,905, filed as application No. PCT/IB2018/056618 on Aug. 30, 2018, now abandoned.

(30) Foreign Application Priority Data

Aug. 31, 2017 (EP) .................................. 17188870

(51) Int. Cl.
A61K 31/454 (2006.01)
A61P 13/12 (2006.01)
(52) U.S. Cl.
CPC ............ *A61K 31/454* (2013.01); *A61P 13/12* (2018.01)
(58) Field of Classification Search
CPC ... A61K 31/4439; A61P 13/12; C07D 401/06; C07D 401/10
See application file for complete search history.

(56) References Cited

U.S. PATENT DOCUMENTS

| 9,682,968 | B2 | 6/2017 | Adams et al. |
| 10,093,663 | B2 | 10/2018 | Adams |
| 11,603,363 | B2 | 3/2023 | Jia et al. |
| 11,723,901 | B2 | 8/2023 | Eder et al. |
| 11,951,101 | B2 | 4/2024 | Baltcheva |
| 2008/0233113 | A1 | 9/2008 | Bansal et al. |
| 2016/0152605 | A1 | 6/2016 | Adams et al. |
| 2023/0265067 | A1 | 8/2023 | Jia |

FOREIGN PATENT DOCUMENTS

| WO | 2014002058 A2 | 1/2014 |
| WO | 2015009616 A1 | 1/2015 |
| WO | 2017/109208 A1 | 6/2017 |

OTHER PUBLICATIONS

Nester et al. "Complement inhibition in C3 glomerulopathy," Seminars in Immunology, 2016, vol. 28, pp. 241-249 (Year: 2016).*
Phillips et al. "Glomerulonephritis associated with acute pneumococcal pneumonia: a case report," Pediatr. Nephrol. 2005, 20: 1494-1495 (Year: 2005).*
Karpman et al., "Complement contribute to the pathogenesis of Shiga toxin-associated hemolytic uremic syndrome", Kidney International, vol. 90, p. 726-739, (2016).
Holers, Complement, Clinical Immunology, 1995, 363-391, chapter 24.
Konar, et al., Eculizumab treatment and impaired opsonophagocytic killing of meningococci by whole blood from immunized adults, Blood, Aug. 17, 2017, 891-899, 130(7).
Lesavre, et al., Mechanism of action of factor D of the alternative complement pathway, J Exp Med., Dec. 1978, 1498-1509, 148.
Volanakis, et al., Renal filtration and catabolismof complement protein D, N Engl J Med., 1985, 395-399, 312(7).
Clinical Trials Study NCT02534909, submitted Nov. 1, 2024, available https://clinicaltrials.gov/study/NCT02534909.
Clinical Trials Study NCT03373461, submitted Jan. 30, 2023, available https://clinicaltrials.gov/study/NCT03373461.
Clinical Trials Study NCT03955445, submitted Oct. 4, 2024, available https://clinicaltrials.gov/study/NCT03955445.
Clinical Trials Study NCT04154787, submitted Oct. 9, 2024, available https://clinicaltrials.gov/study/NCT04154787.
Clinical Trials Study NCT04557462, submitted Oct. 1, 2024, available https://clinicaltrials.gov/study/NCT04557462.
Clinical Trials Study NCT04578834, submitted Oct. 1, 2024, available https://clinicaltrials.gov/study/NCT04578834.
Clinical Trials Study NCT04889430, submitted Oct. 1, 2024, available https://clinicaltrials.gov/study/NCT04889430.
Clinical Trials Study NCT05078580, submitted Jul. 24, 2024, available https://clinicaltrials.gov/study/NCT05086744.
Clinical Trials Study NCT05222412, submitted Jun. 7, 2024, available https://clinicaltrials.gov/study/NCT05086744.
Clinical Trials Study NCT05222412, submitted Oct. 28, 2024, available https://clinicaltrials.gov/study/NCT05222412.
Clinical Trials Study NCT05230537, submitted Jun. 25, 2024, available https://clinicaltrials.gov/study/NCT05230537.
Clinical Trials Study NCT05268289, submitted May 30, 2024, available https://clinicaltrials.gov/study/NCT05268289.
Clinical Trials Study NCT05755386, submitted Oct. 1, 2024, available https://clinicaltrials.gov/study/NCT05755386.
Clinical Trials Study NCT05795140, submitted Oct. 1, 2024, available https://clinicaltrials.gov/study/NCT05795140.
Clinical Trials Study NCT05935215, submitted Nov. 14, 2024, available https://clinicaltrials.gov/study/NCT05935215.
Clinical Trials Study NCT06388941, submitted Oct. 8, 2024, available https://clinicaltrials.gov/study/NCT06388941.
Clinical Trials Study NCT06411626, submitted Jul. 3, 2024, available https://clinicaltrials.gov/study/NCT06411626.
Clinical Trials Study NCT06517758, submitted Nov. 20, 2024, available https://clinicaltrials.gov/study/NCT06517758.

(Continued)

Primary Examiner — Umamaheswari Ramachandran

(57) ABSTRACT

The present invention relates to the novel use of certain piperidinyl-indole derivatives in the treatment of patients suffering from renal diseases or disorders, and in particular for the treatment of patients suffering from C3G (C3 glomerulopathy) and IgAN (IgA nephropathy).

15 Claims, No Drawings

(56) References Cited

OTHER PUBLICATIONS

Clinical Trials Study NCT05842486, submitted May 6, 2024, available https://clinicaltrials.gov/study/NCT05842486?term=NCT05842486&rank=1.

Clinical Trials Study NCT05630001, submitted Nov. 25, 2024, available at https://clinicaltrials.gov/study/NCT05630001?term=NCT05630001&rank=1.

Clinical Trials Study NCT04820530, submitted Oct. 9, 2024, available at https://clinicaltrials.gov/study/NCT04820530?term=NCT04820530&rank=1.

Clinical Trials Study NCT04817618, submitted Aug. 9, 2024, available at https://clinicaltrials.gov/study/NCT04817618?term=NCT04817618&rank=1.

Clinical Trials Study NCT04747613, submitted Oct. 1, 2024, available at https://clinicaltrials.gov/study/NCT04747613?term=NCT04747613&rank=1.

Clinical Trials Study NCT045598918, submitted Oct. 9, 2024, available at https://clinicaltrials.gov/study/NCT04558918?term=NCT04558918&rank=1.

Clinical Trials Study NCT03896152, submitted Jun. 18, 2024, available at https://clinicaltrials.gov/study/NCT03896152?term=NCT03896152&rank=1.

Clinical Trials Study NCT03832114, submitted Jan. 30, 2024, available at https://clinicaltrials.gov/study/NCT03832114?term=NCT03832114&rank=1.

Clinical Trials Study NCT03439839, submitted Jun. 12, 2024, available at https://clinicaltrials.gov/study/NCT03439839?term=NCT03439839&rank=1.

* cited by examiner

USES OF PIPERIDINYL-INDOLE DERIVATIVES

This is a continuation of U.S. application Ser. No. 16/642,905, filed on Feb. 28, 2020, which is a 371 of PCT/IB2018/056618, filed on Aug. 30, 2018, which claims benefit of European Application No. 17188870.4 filed on Aug. 31, 2017, the entire disclosures of which are hereby incorporated by reference.

FIELD OF THE INVENTION

The invention relates to the use of certain piperidinyl-indole derivatives in the treatment of patients suffering from conditions and diseases associated with complement alternative pathway activation such as renal diseases and in particular for the treatment of patients suffering from C3G (C3 glomerulopathy) and IgAN (immunoglobuline A nephropathy).

BACKGROUND OF THE INVENTION

The complement system is an important component of the innate immune system and comprises a cascade of proteases that are normally present in an inactive state. These proteases are organized in three activation pathways: the classical, the lectin, and the alternative pathways that all converge on C3 and C5 cleavage and a common terminal pathway (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertases and the C5-convertases. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The lectin pathway is also calcium and magnesium dependent and is normally stimulated by lectins. The alternative pathway is a magnesium-dependent cascade which is activated by deposition and activation of C3 on certain susceptible surfaces (e.g., cell wall polysaccharides of yeast and bacteria, and certain biopolymer materials). In addition to alternative pathway-specific stimulation, the alternative pathway also serves as an amplification loop for the other complement pathways.

Factor B is a key protease of the alternative pathway and may be a suitable target for the inhibition of the alternative pathway as well as the amplification of the other complement pathways. Its plasma concentration in humans is typically about 300 µg/mL (or about 3 µM), and it has been shown to be a critical enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

WO2017/109208 discloses certain polypeptides for inhibiting complement activation and their use in disorders such as atypical hemolytic uremic syndrome (aHUS), C3G and IgA nephropathy. It describes a fusion construct in which multiple active domains from naturally occurring complement regulators (complement factor H (FH) and complement FH related protein 1 (FHR1)) were combined to a single molecule. The FH part of the molecule dissociates the C3 convertase of the AP, and at the same time acts as a cofactor of Complement factor I, which cleaves C3b to smaller, inactive fragments. In addition, the fusion construct also binds to C5 and inhibits the (AP) C5 convertase. Finally, the FHR1-part of the construct inhibits the classical complement pathway (CP), as shown in the Wieslab assay for classical pathway activity. Therefore this should result in a dual inhibition of the classical pathway and the alternative pathway/amplification loop. WO2015/009616 describes the synthesis and some utilities of the piperidinyl-indole derivatives. The said compounds are powerful factor B inhibitors and suppress the amplification of the complement system caused by C3 activation irrespective of the initial mechanism of activation (including for example activation of the classical, lectin or alternative pathways). WO2015/009616 discloses a wide variety of indications including the renal diseases atypically hemolytic uremic syndrome (aHUS) and glomerulonephritis including membrane proliferative glomerulonephritis. It is silent about the use of the piperidinyl-indole derivatives in other renal diseases which are separate conditions with a distinctly different causality from the above, in particular it does not describe the use in classical HUS (E. coli induced hemolytic uremic syndrome) and membraneous nephropathy. In contrast to the polypeptide construct according to WO2017/109208, the low molecular weight compounds as disclosed in WO2015/009616 specifically inhibit the protease complement factor B, which is responsible for cleaving C3 and C5 of the AP. Thereby the direct generation of C3a, C5a and C5b-9 through the classical pathway is spared. In 2017, Konar and Dranoff (Konar M and Granoff D M 2017. Eculizumab treatment and impaired opsonophagocytic killing of meningococci by whole blood from immunized adults. Blood. 130(7):891-899) have elegantly shown that selective inhibition of Factor D, the protease that activates FB, did not impair the protective immune response against N. meningitidis in vaccinated individuals, whereas inhibition at the level of C5 does.

SUMMARY OF THE INVENTION

Surprisingly, the present invention provides now a method of treating or preventing factor B mediated diseases, which consists of administering a compound of Formula (I) to a patient suffering from a renal disease or disorder selected from the complement-driven renal disease C3G (C3 glomerulopathy) and IgAN (immunoglobuline A nephropathy) and other nephropathies with evidence of glomerular C3 deposition such as MN (membranous nephropathy) and HUS (E. coli induced hemolytic uremic syndrome).

DETAILED DESCRIPTION OF THE INVENTION

In a first embodiment, the invention provides a compound of formula (I) or a pharmaceutically acceptable salt thereof, for use in the treatment of the complement-driven renal diseases C3G (C3 glomerulopathy), IgAN (immunoglobuline A nephropathy) and other nephropathies with evidence of glomerular C3 deposition such as MN (membranous nephropathy) and HUS (E. coli induced hemolytic uremic syndrome). Compounds of Formula (I) or pharmaceutically acceptable salts thereof, are represented by the following structure:

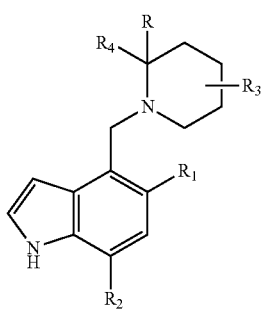

Wherein
R is hydrogen, $C_1$-$C_4$alkyl, or $C_1$-$C_6$alkoxy;
$R^1$ is $C_1$-$C_6$alkoxy;
$R^2$ is $C_1$-$C_6$alkyl;
$R^3$ is $C_1$-$C_6$alkoxy; $C_1$-$C_6$alkyl; or hydroxyl;
$R^4$ is phenyl, optionally substituted by —C(O)$R^8$, and
$R^8$ is hydroxy, $C_1$-$C_4$alkoxy, or amino.

In a second embodiment, the invention provides compounds or pharmaceutically acceptable salts thereof for use in accordance to the first embodiment, wherein
R is hydrogen; or $C_1$-$C_2$alkyl;
$R^1$ is $C_1$-$C_6$alkoxy;
$R^2$ is $C_1$-$C_6$alkyl;
$R^3$ is $C_1$-$C_6$alkoxy; or $C_1$-$C_6$alkyl; and
$R^4$ is phenyl, optionally substituted by —C(O)$R^8$, and $R^8$ is hydroxyl or $C_1$-$C_4$alkoxy.

In a third embodiment, the invention provides compounds or pharmaceutically acceptable salts thereof for use in accordance to the first embodiment wherein
R is hydrogen;
$R^1$ is $C_1$-$C_2$alkoxy;
$R^2$ is $C_1$-$C_2$alkyl;
$R^3$ is $C_1$-$C_2$alkoxy; and
$R^4$ is phenyl, optionally substituted by —C(O)$R^8$, and $R^8$ is hydroxy.

In a forth embodiment, the invention provides compounds for use in accordance to the first embodiment, wherein the compound or a pharmaceutically acceptable salt thereof is selected from the group consisting of:
4-(1-((5-methoxy-7-methyl-1H-indol-4-yl)methyl)-4-methylpiperidin-2-yl)benzoic acid;
4-(4-methoxy-1-((5-methoxy-7-methyl-1H-indol-4-yl)methyl)piperidin-2-yl)benzoic acid;
4-(4-ethoxy-1-((5-methoxy-7-methyl-1H-indol-4-yl)methyl)piperidin-2-yl)benzoic acid;
4-(5-methoxy-1-((5-methoxy-7-methyl-1H-indol-4-yl)methyl)piperidin-2-yl)benzoic acid;
4-(5-hydroxy-1-((5-methoxy-7-methyl-1H-indol-4-yl)methyl)piperidin-2-yl)benzoic acid;
4-ethyl-1-((5-methoxy-7-methyl-1H-indol-4-yl)methyl)piperidin-2-yl-benzoic acid;
4-(ethyl-1-((5-methoxy-7-methyl-1H-indol-4-yl)methyl)piperidin-2-yl)benzoic acid;
ethyl 4-((2S,4R)-1-((5-methoxy-7-methyl-1H-indol-4-yl)methyl)-4-methylpiperidin-2-yl)benzoate; and
ethyl 4-((2S,4S)-4-ethoxy-1-((5-methoxy-7-methyl-1H-indol-4-yl)methyl)piperidin-2-yl)benzoate.

In a fifth embodiment, the invention provides a compound for use in accordance to the first embodiment, wherein the compound or a pharmaceutically acceptable salt thereof is 4-((2S,4S)-4-ethoxy-1-((5-methoxy-7-methyl-1H-indol-4-yl)methyl)piperidin-2-yl)benzoic acid.

In a sixth embodiment the invention relates to a method of treating or preventing C3G (C3 glomerulopathy), IgAN (immunoglobuline A nephropathy) or other nephropathies with evidence of glomerular C3 deposition such as MN (membranous nephropathy) and HUS (*E. coli* induced hemolytic uremic syndrome), in patient suffering therefrom, which consists of administering an effective amount of a compound of formula (I) or a pharmaceutically acceptable salt thereof in accordance to anyone of the definitions of the embodiments 1, 2, 3, 4 or 5 to a patient suffering therefrom.

In a further embodiment, the invention provides a compound for use in accordance to any one of claims 1-5, wherein the use is in the treatment of C3G (C3 glomerulopathy).

In a further embodiment, the invention provides a compound for use in accordance to any one of claims 1-5, wherein the use is in the treatment of IgAN (immuneglobuline A nephropathy).

In a further embodiment, the invention provides a compound for use in accordance to any one of claims 1-5, wherein the use is in the treatment of MN (membranous nephropathy).

In a further embodiment, the invention provides a compound for use in accordance to any one of claims 1-5, wherein the use is in the treatment of HUS (*E. coli* induced hemolytic uremic syndrome).

In a further embodiment the invention relates to a pharmaceutical composition comprising a therapeutically effective amount of a compound of formula (I) or a pharmaceutically acceptable salt thereof in accordance to the definition of embodiment 1 and one or more pharmaceutically acceptable carriers, for use in the treatment of a disease or disorder selected from of C3G (C3 glomerulopathy), IgAN (immunoglobuline A nephropathy) and other nephropathies with evidence of glomerular C3 deposition such as MN (membranous nephropathy) and HUS (*E. coli* induced hemolytic uremic syndrome).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

Pharmaceutically acceptable acid addition salts may be formed with inorganic acids and organic acids.

Pharmaceutically acceptable base addition salts may be formed with inorganic and organic bases.

Representative examples of pharmaceutically acceptable salts of compounds of formula (I) were already described in WO2015/009616 and are likewise suitable for this invention.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or a biological process (e.g., tissue regeneration and reproduction) (i) mediated by Factor B, or (ii) associated with Factor B activity, or (iii) characterized by activity (normal or abnormal) of the complement alternative pathway; or (2) reducing or inhibiting the activity of Factor B; or (3) reducing or inhibiting the expression of Factor B; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor B and/or the complement alternative pathway; or at least partially reducing or inhibiting the expression of Factor B and/or the complement alternative pathway. The meaning of the term "a therapeutically effective amount" as illustrated in the above embodiment for Factor B and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein the use of a compound of the present invention may be in the form of one of the possible isomers such as rotamers, atropisomers, tautomers or mixtures thereof, for example, as substantially pure geometric (cis or trans) isomers, diastereomers, optical isomers (antipodes), racemates or mixtures thereof. For clarity, positional isomer are not encompassed by the above.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Prophylactic and Therapeutic Uses

In another embodiment, the present invention provides methods of treating a renal disease or disorder, comprising administering to a subject in need of such treatment an effective amount of a compound or a pharmaceutically acceptable salt thereof in accordance to the definition of any one of embodiments 1-5, wherein said disease or disorder is selected from C3G, IgAN and other nephropathies with evidence of glomerular C3 deposition.

Compounds of formula (I) or pharmaceutically acceptable salts thereof may be administered in unit dosage of about 0.1-1000 mg of active ingredient(s) for a subject of about 50-70 kg, or about 0.1-500 mg or about 0.1-250 mg or about 0.1-150 mg or about 0.5-100 mg, or about 0.5-50 mg of active ingredients. The therapeutically effective dosage thereof, may depend on the species of the subject, the body weight, age and individual condition, the disorder or disease or the severity thereof being treated. A physician, clinician or veterinarian of ordinary skill may readily determine the effective amount of each of the active ingredients necessary to prevent, treat or inhibit the progress of the disorder or disease.

The efficacy of a compound according to embodiment 1 may be assessed by the following methods:

1. Clinical Trials for Complement Driven Renal Disease; Specifically IgAN

Patients are recruited in accordance to the following criteria:
- Adult IgAN patients diagnosed within 2 years
- Fulfilling diagnostic criteria as high risk of fast progression such as high blood pressure and/or on antihypertensives and >1 g/d proteinuria
- Renal biopsy=IgAN, including IgAN with vasculitis
- eGFR (glomerular filtration rate) is >40 and <100 ml/min/1.73 m$^2$
- Supportive care (incl. diuretic, ACE (Angiotensin Converting Enzyme) inhibitors, ARB (Angiotensin Renin Blocker), statins) to be maintained in trial.
- Randomization after run-in period.

For the trial patients are vaccinated to eliminate the risk of infections caused by encapsulated organisms, including *Streptococcus pneumoniae*, *Neisseria meningitidis*, and *Haemophilus influenzae*. Vaccination may be effected for example with 23-valent polysaccharide (PS) vaccine, or with heptavalent protein-polysaccharide conjugate (PCV-7) vaccine.

Pursuant to vaccination, patients are then treated with a daily dosage of a compound of formula (I) of 25, 50, 100 and 200 mg given twice per day (BID). The blood pressure is monitored per standard practice and proteinuria is determined by regularly determining the low molecular weight proteins in the urine, such as albumines and globulines.

The duration of treatment with a compound of formula (I) is at least 3 months, and the primary endpoints for an effective treatment is achieved with a reduction of urine protein creatinine ratio (UPCR) being 25% or more.

As secondary endpoints, a renal histology is carried out in selected patients, wherein a reduced complement activation, less inflammation, reduced mesangial expansion is aimed at in the histological scores.

2. Clinical Trials for Complement Driven Renal Disease, Specifically C3G:

Patients are recruited in accordance to the following criteria:
- Adult patients diagnosed with C3G
- Renal biopsy evidencing C3G (confirmed results within 3 months)
- Patients with low serum C3 (convertase) or FB (factor B) levels and any level of GFR (Glomerular Filtration Rate)
- GFR≥40 ml/min/1.73 m$^2$
- Supportive care (incl. diuretic, ACE inhibitors, ARB, statins) to be maintained in trial.
- Randomization after run-in period For the trial, patients are vaccinated to eliminate the risk of infections caused by encapsulated organisms, including *Streptococcus pneumoniae*, *Neisseria meningitidis*, and *Haemophilus influenzae*. Vaccination may be effected for example with 23-valent polysaccharide (PS) vaccine, or with heptavalent protein-polysaccharide conjugate (PCV-7) vaccine.

Pursuant to vaccination, patients are then treated with a daily dosage of a compound of formula (I) of 25, 50, 100 and 200 mg given twice per day (BID).

The duration of treatment with a compound of formula (I) is at least 2 months.

The primary endpoint for an effective treatment is achieved if proteinuria is reduced by more than 25%.

A secondary endpoint for an effective treatment is an improved eGFR as well as an improved histology in renal biopsy, target effects in tissue after 3 months of treatment (if possible, after 6 months of therapy).

Compounds of formula (I) or pharmaceutically acceptable salts thereof as disclosed in embodiments 1-5 are potent inhibitors of factor B and are tested in the clinical trials (1) and (2) described above.

Experimental Part:

1. Inhibition of Complement Dysregulation was Measured by Immunofixation Electrophoresis (described by Zhang et al., Clin J Am Soc Nephrology 7, pp 265-274 (2012)).

This assay is based on stabilized C3 convertase in patient serum. Patient serum is mixed 1:1 with normal serum and incubated for 30 minutes at 37° C. Normal serum serves as source for C3, since patient C3 levels can be very low. Outcome is the proportion of C3 that is cleaved vs uncleaved C3. Maximal cleavage was determined by incubating serum in Mg$^{2+}$ EGTA-PBS, background cleavage was determined by incubating the serum in EDTA-PBS. Inhibition by a test compound was calculated by the following formula:

(Cleavage in presence of test compound−background cleavage)/(maximal cleavage−background cleavage)

The assay was performed in samples of 9 patients with C3G with the following causes for alternative pathway (AP) dysregulation:
- C3Nef (autoantibodies stabilizing C3 convertase) in 3 patients
- Autoantibodies against FH (factor H) in 2 patients
- Unknown cause in 2 patients
- Autoantibodies against FB (factor B) in 2 patients.

Samples of patients with both C3G (C3 glomerulonephritis) and DDD (dense deposit disease) were included.

In this assay, we tested the compounds of embodiment 4. For example, the compound of embodiment 5 inhibited C3 cleavage at a concentration of 3.3 micromolar by >97%, and in the presence of 1.1 micromolar by 63%.

2. Inhibition of Preformed C3 Convertase that is Stabilized by C3Nefs or FB Autoantibodies Inhibition of the preformed and stabilized C3 convertase was measured by C3 Convertase Stabilizing Assay (C3CSA) (described by Zhang et al., Clin J Am Soc Nephrology 7, pp 265-274 (2012)). In this assay, C3 convertase is artificially constructed on the surface of sheep erythrocytes. While C3 convertase normally has a half-life of 90 seconds at 37° C., the decay is delayed by addition of IgG purified from patients. Compounds were added at the same time as the patient derived IgG in order to inhibit convertase stabilization/convertase activity and allow its decay. After IgG (and compound) administration, convertase was allowed to decay for 15 minutes at 30° C. Then, rat serum in EDTA was added for 30 minutes at 37° C. to allow the stabilized C3 convertases to activate the terminal complement pathway and lyse the erythrocytes. Erythrocyte lysis is associated with hemoglobin release and therefore was quantified via absorption in the supernatant at 415 nm. Maximal hemolysis was determined by lysis at time 0 and as a background, hemolysis in EDTA buffer (full inhibition of all complement pathways) was measured.

Inhibition of the stabilized C3 convertase was measured using IgGs from 15 patients with C3G, wherein 7 patients had DDD and 8 patients had C3GN. Four of the patients had antibodies directed against FB, and 11 patients had C3 nephritic factors, i.e. antibodies directed against the C3 convertase. The compound of embodiment 5 inhibited hemolysis of the C3-convertase-loaded erythrocytes by >99% compared to the level observed in the presence of EDTA (no complement activity) at compound concentrations of 0.15 micromolar.

3. Inhibition of C3 Deposition on Human Microvascular Endothelial Cells Stimulated with Serum Derived from Patients with Shiga-Toxin Producing *E. Coli*-Induced Hemolytic Uremic Syndrome (STEC-HUS or Classical HUS)

As described in Morigi et al., 2011 (Morigi M, Galbusera M, Gastoldi S, Locatelli, M, Buelli, S, Pezzotta A, Pagani C, Noris M, Gobbi M, Stravalaci M, Rottoli D, Tedesco F, Remuzzi G and Joja C: 2011. Alternative pathway activation of complement by Shiga toxin promotes exuberant C3a formation that triggers microvascular thrombosis. J Immunol. 187(1):172-80), human microvascular endothelial cell line of dermal origin (HMEC-1, ATCC CRL-3243) were plated on glass slides and used when confluent. Cells were activated with 10 µM ADP for 10 minutes and then incubated for 4 hours with serum (collected from 3 STEC-HUS patients during the acute phase of the disease or healthy controls) diluted 1:2 with test medium (HBSS with 0.5% BSA), in the presence or in the absence of the CFB inhibitor of embodiment 5 at 2 different concentrations (1 and 10 microM). At the end of the incubation step HMEC-1 were treated with fluorochrome-conjugated anti-human C3c. In each experiment, a pool of sera from healthy controls was tested in parallel with patient serum. A confocal inverted laser microscope was used for acquisition of the fluorescent staining on endothelial cell surface.

Fifteen fields per sample were acquired and the area occupied by the fluorescent staining was evaluated by automatic edge detection using built-in specific functions of the software Image J and expressed as pixel2 per field analyzed. The highest and lowest values were discarded and the mean±SE was calculated on the remaining 13 fields.

Results: Serum from patients with acute STEC-HUS induced a massive C3 deposition on ADP-activated endothelial cells in respect to sera from healthy controls (P<0.0001). The presence of the CFB inhibitor of embodiment 5 in serum of STEC-HUS patients induced a dose-response decrease of C3 deposition on ADP-activated HMEC.-1 (73% reduction for 1 microM and 89% reduction for 10 microM, p<0.0001 for both). Notably the amount of C3 deposits on endothelial cells exposed to STEC-HUS serum added with the CFB inhibitor of embodiment 5 at 10 microM concentration did not significantly differ from C3 deposits observed on cells exposed to control sera.

4. FB Inhibitor Prevents the Development and Progression of Passive Heymann Nephritis in Rats Passive Heymann nephritis in the rat is the most common animal model for membranous nephropathy (see Jefferson J A, Pippin J W and Shankland S J 2010. Experimental Models of membranous nephropathy. Drug Discov Today Dis Models. 7(1-2):27-33). It is induced by the transfer of a polyclonal serum derived from rabbits immunized with rat megalin and manifests inflammatory changes in the kidney that are highly reminiscent with the human disease. Significant proteinuria is observed 4 days after the antibody transfer and increases until 2 weeks post transfer.

Prophylactic treatment with the Factor B inhibitor of embodiment 5 (twice daily oral gavage, 20 or 60 mg/kg/d) significantly reduced proteinuria at 14 days post transfer by 82% or 75% (p<0.0001) and significantly reduced histopathological changes (combined scores are 2.2, 0.3 and 0.4 for vehicle and the FB inhibitor of embodiment 5 at 20 and 60 mg/kg, respectively, p<0.005). Moreover, in a separate experiment, therapeutic treatment with 60 mg/kg of the FB inhibitor of embodiment 5 (twice daily oral gavage) starting after manifestation of proteinuria (6 days post serum transfer) blocked further progression of the disease. Proteinuria increased from 0.79 on day 6 to 1.93 on day 14 in the control group, but remained stable in the group treated with the FB inhibitor of embodiment 5 (0.74 and 0.81 on days 6 and 14, respectively. The combined histopathology scores was reduced from 2.7 in the vehicle-treated group to 1.1 in the FB inhibitor-treated group, p<0.005).

The invention claimed is:

1. A method of treating C3 glomerulopathy (C3G), in a patient suffering therefrom, comprising the step of administering at a dose of 200 mg given twice per day of a compound of formula (I) or a pharmaceutically acceptable salt thereof to the patient, wherein

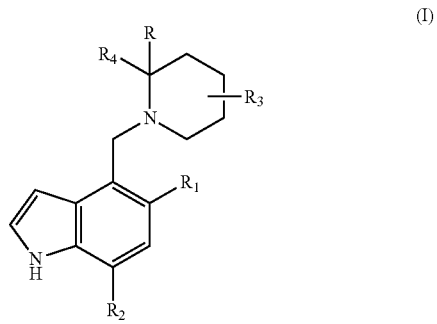

(I)

R is hydrogen, $C_1$-$C_4$alkyl, or $C_1$-$C_6$alkoxy;
$R^1$ is $C_1$-$C_6$alkoxy;
$R^2$ is $C_1$-$C_6$alkyl;
$R^3$ is $C_1$-$C_6$alkoxy; $C_1$-$C_6$alkyl; or hydroxyl;
$R^4$ is phenyl, optionally substituted by —C(O)$R^8$, and $R^8$ is hydroxy, $C_1$-$C_4$alkoxy, or amino.

2. The method of claim 1, wherein
R is hydrogen or $C_1$-$C_2$alkyl;
$R^1$ is $C_1$-$C_6$alkoxy;
$R^2$ is $C_1$-$C_6$alkyl;
$R^3$ is $C_1$-$C_6$alkoxy or $C_1$-$C_6$alkyl; and
$R^4$ is phenyl, optionally substituted by —C(O)$R^8$, and $R^8$ is hydroxyl or $C_1$-$C_4$alkoxy.

3. The method of claim 1, wherein
R is hydrogen;
$R^1$ is $C_1$-$C_2$alkoxy;
$R^2$ is $C_1$-$C_2$alkyl;
$R^3$ is $C_1$-$C_2$alkoxy; and
$R^4$ is phenyl, optionally substituted by —C(O)$R^8$, and $R^8$ is hydroxy.

4. The method of claim 1, wherein the compound of formula (I) is selected from the group consisting of:

4-(1-((5-methoxy-7-methyl-1H-indol-4-yl)methyl)-4-methylpiperidin-2-yl)benzoic acid;

4-(4-methoxy-1-((5-methoxy-7-methyl-1H-indol-4-yl)methyl)piperidin-2-yl)benzoic acid;

4-(4-ethoxy-1-((5-methoxy-7-methyl-1H-indol-4-yl)methyl)piperidin-2-yl)benzoic acid;

4-(5-methoxy-1-((5-methoxy-7-methyl-1H-indol-4-yl)methyl)piperidin-2-yl)benzoic acid;

4-(5-hydroxy-1-((5-methoxy-7-methyl-1H-indol-4-yl)methyl)piperidin-2-yl)benzoic acid;

ethyl 4-((2S,4R)-1-((5-methoxy-7-methyl-1H-indol-4-yl)methyl)-4-methylpiperidin-2-yl)benzoate; and ethyl 4-((2S,4S)-4-ethoxy-1-((5-methoxy-7-methyl-1H-indol-4-yl)methyl)piperidin-2-yl)benzoate.

5. The method of claim 1, wherein proteinuria in the patient is reduced by more than 25% after treatment.

6. The method of claim 1, wherein eGFR in the patient is improved after treatment.

7. The method of claim 1, wherein the patient is vaccinated against *Neisseria meningitidis, Streptococcus pneumoniae* or *Haemophilus influenzae* prior to treatment.

8. A method of treating C3 glomerulopathy (C3G), in a patient suffering therefrom, comprising the step of administering at a dose of 200 mg given twice per day of 4-((2S,4S)-4-ethoxy-1-((5-methoxy-7-methyl-1H-indol-4-yl)methyl)piperidin-2-yl)benzoic acid or a pharmaceutically acceptable salt thereof.

9. The method of claim 1, wherein the treatment comprises reducing the urine protein creatinine ratio (UPCR) as compared to baseline.

10. The method of claim 1, wherein the treatment comprises reducing the UPCR by 25% or more as compared to baseline.

11. The method of claim 8, wherein the treatment comprises reducing the urine protein creatinine ratio (UPCR) as compared to baseline.

12. The method of claim 8, wherein the treatment comprises reducing the UPCR by 25% or more as compared to baseline.

13. The method of claim 8, wherein proteinuria in the patient is reduced by more than 25% after treatment.

14. The method of claim 8, wherein eGFR in the patient is improved after treatment.

15. The method of claim 8, wherein the patient is vaccinated against *Neisseria meningitidis, Streptococcus pneumoniae* or *Haemophilus influenzae* prior to treatment.

* * * * *